United States Patent
Maekawa et al.

(10) Patent No.: US 7,409,242 B2
(45) Date of Patent: Aug. 5, 2008

(54) ACTIVE MUSCLE DISPLAY DEVICE

(75) Inventors: Satoshi Maekawa, Koganei (JP); Yoshihisa Fujiwara, Koganei (JP); Manabu Kotani, deceased, late of Ashiya (JP); by Hiroko Kotani, legal representative, Ashiya (JP); Takahiko Arimoto, Akashi (JP)

(73) Assignee: National Institute of Information and Communications Technology, Tokyo (JP)

( * ) Notice: Subject to any disclaimer, the term of this patent is extended or adjusted under 35 U.S.C. 154(b) by 243 days.

(21) Appl. No.: 10/527,087

(22) PCT Filed: Sep. 11, 2002

(86) PCT No.: PCT/JP02/09302

§ 371 (c)(1),
(2), (4) Date: Nov. 14, 2005

(87) PCT Pub. No.: WO2004/023996

PCT Pub. Date: Mar. 25, 2004

(65) Prior Publication Data

US 2006/0129057 A1    Jun. 15, 2006

(51) Int. Cl.
*A61B 5/04* (2006.01)
(52) U.S. Cl. .................................................. 600/546
(58) Field of Classification Search ................ 600/546, 600/511, 300; 607/45
See application file for complete search history.

(56) References Cited

U.S. PATENT DOCUMENTS

2005/0240242 A1* 10/2005 DiLorenzo ................... 607/45
2005/0267376 A1* 12/2005 Marossero et al. .......... 600/511

OTHER PUBLICATIONS

T. Arimoto et al.; The Institute of Electronics, Information and Communication Engineers, Gijutsu Kenkyu Hokoku, Mar. 12, 2002, vol. 101, No. 736, pp. 159-166. Cited in Int'l. search.
H. Nakamura et al.; BME, May 10, 2002, vol. 16, No. 5, pp. 32-37. Cited in the Int'l. search report.

\* cited by examiner

*Primary Examiner*—Brian Szmal
(74) *Attorney, Agent, or Firm*—Westerman, Hattori, Daniels & Adrian, LLP.

(57) ABSTRACT

In order to provide an active muscle display unit that extracts a firing pattern of the individual motor unit without applying a load to living organisms and display the extracted motor unit, the active muscle display unit comprises multiple electrodes that are arranged on a skin surface, a surface electromyogram measuring part that measures a surface electromyogram on the skin surface at the multiple electrodes, a motor unit separating part that estimates the individual motor unit constituting an active muscle based on the surface electromyogram measured by the surface electromyogram measuring part, a motor unit position estimating part that estimates a three-dimensional position of the firing motor unit based on the motor unit estimated to be the firing motor unit by the motor unit separating part, and a display part that displays the motor unit estimated by the motor unit position estimating part in an image.

13 Claims, 14 Drawing Sheets impulse response of mixing filter to fourth independent component

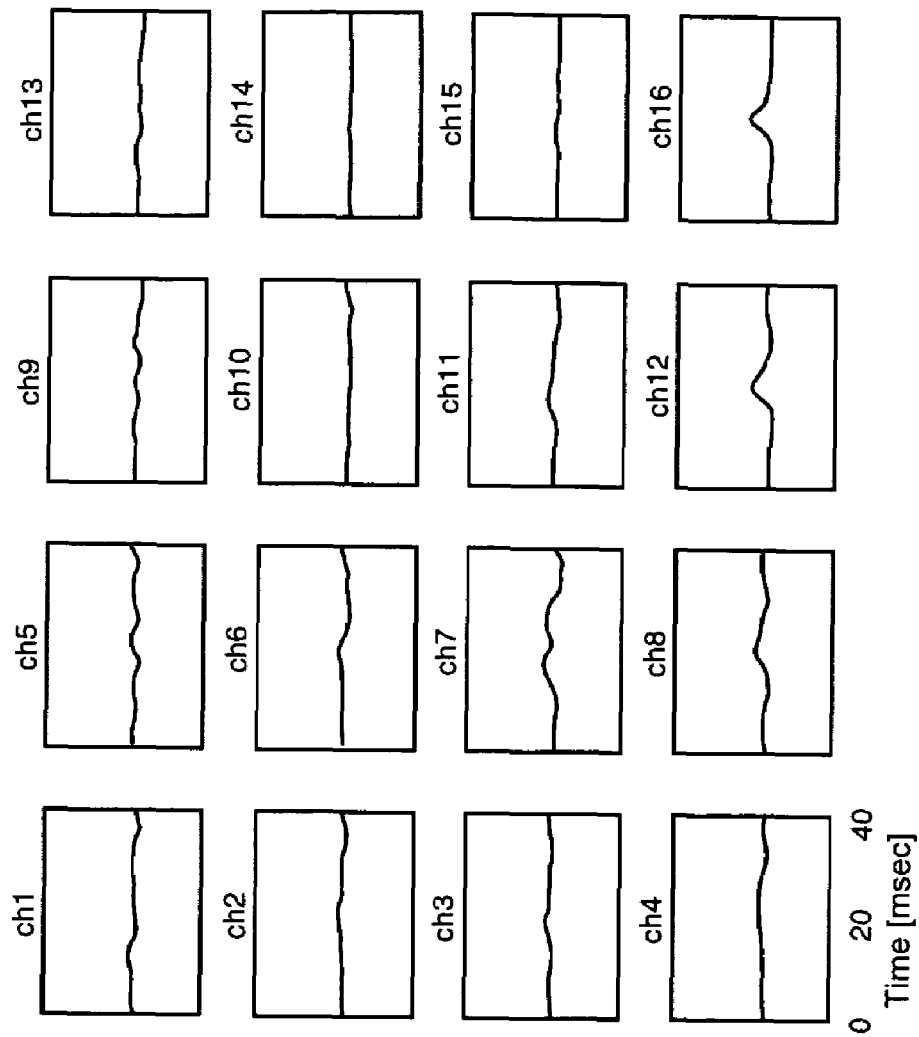

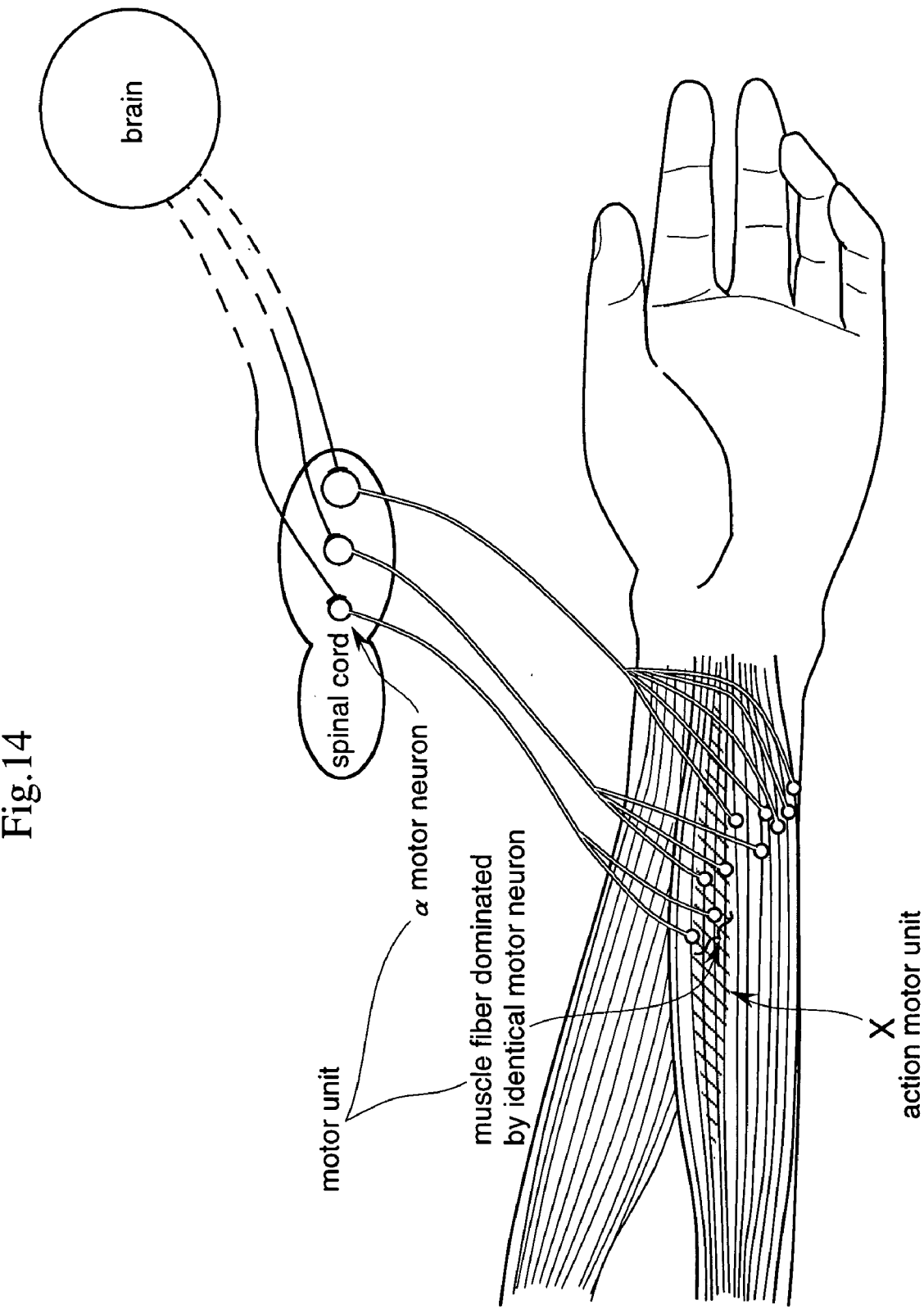

ACTIVE MUSCLE DISPLAY DEVICE

FIELD OF THE ART

This invention relates to an active muscle display unit that extracts a motor unit constituting a muscle from a surface electromyogram measured on a skin surface and displays an active muscle based on the extracted motor unit.

BACKGROUND ART

Living organisms conduct complicated motor control, and then it is very significant to clarify the control mechanism in a field of ergonomics or the like. A lot of approaches to measure and analyze the nerve-muscle action have been tried in order to elucidate the control mechanism in vivo.

Muscles consist of multiple sub-units referred to as motor units. The motor unit consists of a single α motor neuron (hereinafter referred to as α-MN) in a spinal cord and a muscle fiber group dominated by the α-MN, and is a minimum function unit of a nerve-muscle control mechanism. When the muscle contracts, the multiple motor units act in a cooperative manner. In order to elucidate the nerve-muscle control mechanism it is important to measure a motor unit action potential (hereinafter referred to as an MUAP) and to analyze each action style.

An electromyogram showing a change of an electric potential generating in accordance with contraction of muscle is measured as an interference waveform of multiple MUAPs. There are a needle electromyogram measured by the use of needle electrodes stinging in muscles and a surface electromyogram measured by the use of non-invasive surface electrodes as the electromyogram.

Since the needle electromyogram has merits such that it is not susceptible to living organism tissue and it can separate the motor unit relatively easily, the needle electromyogram is used for analyzing the electromyogram by separating it into the motor units. (K. C. McGill, K. L. Cummins, and L. J. Dorfman, "Automatic Decomposition of Clinical Electromyogram", IEEE Trans. Biomed. Eng. BME, vol. 32, pp. 470-477, 1985) Since the surface electromyogram can be measured by attaching surface electrodes to a surface of skin, it has a merit that the surface electromyogram can be measured relatively easily compared with the needle electromyogram.

However, since it is necessary for the needle electromyogram to sting needle electrodes on muscles in order to measure the electromyogram and there is a problem that load is applied to living organisms, it has been difficult to measure multiple muscles at a time. In addition, a portion where the needle electrodes measure is a very narrow range, and which portion is to be measured in a tissue of a living organism has to be settled previously. Meanwhile, since the surface electromyogram monitors multiple MUAPs locating under the electrodes in a spatially and temporally added state, it is difficult to extract a firing pattern of an individual motor unit.

DISCLOSURE OF THE INVENTION

In order to solve the above-mentioned problems, the present claimed invention devices a following means.

The present claimed invention is characterized by comprising multiple electrodes that are arranged on a skin surface, a surface electromyogram measuring part that measures a surface electromyogram on the skin surface at the multiple electrodes, a motor unit separating part that separates a signal from an individual motor unit constituting an active muscle based on the surface electromyogram measured by the surface electromyogram measuring part, a motor unit position estimating part that estimates a three-dimensional position of the motor unit based on a potential distribution on the skin surface generating due to action of the individual motor unit obtained by the motor unit separating part, and a display part that displays action of the individual the motor unit extracted by the motor unit position estimating part collectively in an image.

In accordance with this arrangement, since the surface electromyogram can be measured by multiple surface electrodes and the surface electromyogram measuring part without invading the living organisms, a three dimensional position of the active motor unit can be extracted from the multiple spatially and temporally added MUAPs by the motor unit separating part and the motor unit position estimating part, and the extracted motor unit can be displayed in an image by the display part, the active muscle display unit is very useful for analyzing a control mechanism of a muscle in living organisms.

In order to estimate an individual motor unit that shows a predetermined firing pattern from the surface electromyogram measured by the surface electromyogram measuring part, it is preferable that the motor unit separating part separates an individual motor unit that shows the predetermined firing pattern from the surface electromyogram measured by the surface electromyogram measuring part based on a multichannel blind deconvolution method.

In order to extract the active motor unit more accurately, it is preferable that a motor unit firing pattern storing part that stores a distribution pattern of a firing interval and a surface electromyogram waveform of the motor unit based on physiological knowledge is comprised, and a time-series signal of each electrodes separated by the motor unit separating part is checked against the motor unit whose distribution pattern of the firing interval and the surface electromyogram waveform are stored, and if a distribution pattern of a firing interval and a surface electromyogram waveform of the time-series signal coincide with the stored distribution pattern of the firing interval and the stored surface electromyogram waveform, the time-series signal is specified as the motor unit.

It is necessary for the motor unit position estimating part to estimate a current source flowing in a tissue of the living organisms or a potential distribution formed by depolarization of a muscle fiber necessary to reproduce the given potential distribution on the skin surface. In order to make estimation, it is preferable that the motor unit position estimating part solves an inverse problem provided that a potential at a position of the surface electrode given by the motor unit separating part is a boundary condition in accordance with a partial differential equation that gives an electrostatic field.

As a more preferable state of the present claimed invention it is represented that the motor unit position estimating part estimates a current source by the use of the Poisson's equation to reproduce its potential based on an electrode position potential corresponding to an individual motor unit obtained by the motor unit separating part.

In addition, in order to solve the inverse problem for the motor unit position estimating part, it is necessary to comprise a conductance distribution model storing part that stores a conductance distribution model wherein distribution and an arrangement of fat, bone, and muscle whose electrical conductance differs respectively in vivo are modeled.

In addition, since the inverse problem for the motor unit position estimating part is an ill-posed problem itself, in order to solve the inverse problem uniquely, it is necessary to comprise a motor unit depolarization model storing part that stores a depolarization model of the motor unit.

In order to improve accuracy of separation, it is preferable that the above-mentioned multiple electrodes are arranged in an array.

In order to preferably remove disturbance such as a change of a contact resistance due to a movement of a skin and a fluctuation of a low frequency generating due to a swinging movement of the lead wires, it is preferable that a high-pass filter that passes a signal having a frequency component not less than a predetermined frequency is arranged and the surface electromyogram measured by the surface electromyogram measuring part is passed through the high-pass filter.

In order to conduct the multi-channel blind deconvolution with accuracy, it is preferable that the surface electromyogram measured by the surface electromyogram measuring part is normalized to an average 0, and a distribution 1, or that the motor unit separating part learns the surface electromyogram measured by the surface electromyogram measuring part under a predetermined condition and estimates the individual motor unit constituting the firing muscle based on the learned electromyogram.

In addition, if a muscle distribution model storing part that stores a muscle distribution model wherein a muscle fiber or a motor neuron constituting the motor unit is modeled is arranged and the display part three-dimensionally displays the motor unit extracted by the motor unit position estimating part in a state overlapped with the muscle distribution model, it is possible to recognize a movement of the firing motor unit more concretely.

In order to measure the surface electromyogram with accuracy, it is preferable that a measurement monitoring part that outputs the surface electromyogram during measurement in an image while the surface electromyogram is measured is arranged and in case that the surface electromyogram that is estimated to be other than the motor unit is output in an image by the measurement monitoring part, the surface electromyogram measuring part is set not to conduct the measurement.

BRIEF DESCRIPTION OF THE DRAWINGS

FIG. 13 is a view showing an impulse response of the mixing filter to a sixteenth independent component in accordance with this embodiment.

FIG. 14 is a view showing a mode to display a firing motor unit in an image in accordance with this embodiment.

BEST MODES OF EMBODYING THE INVENTION

One embodiment of the present claimed invention will be explained with reference to drawings.

Figure 1:
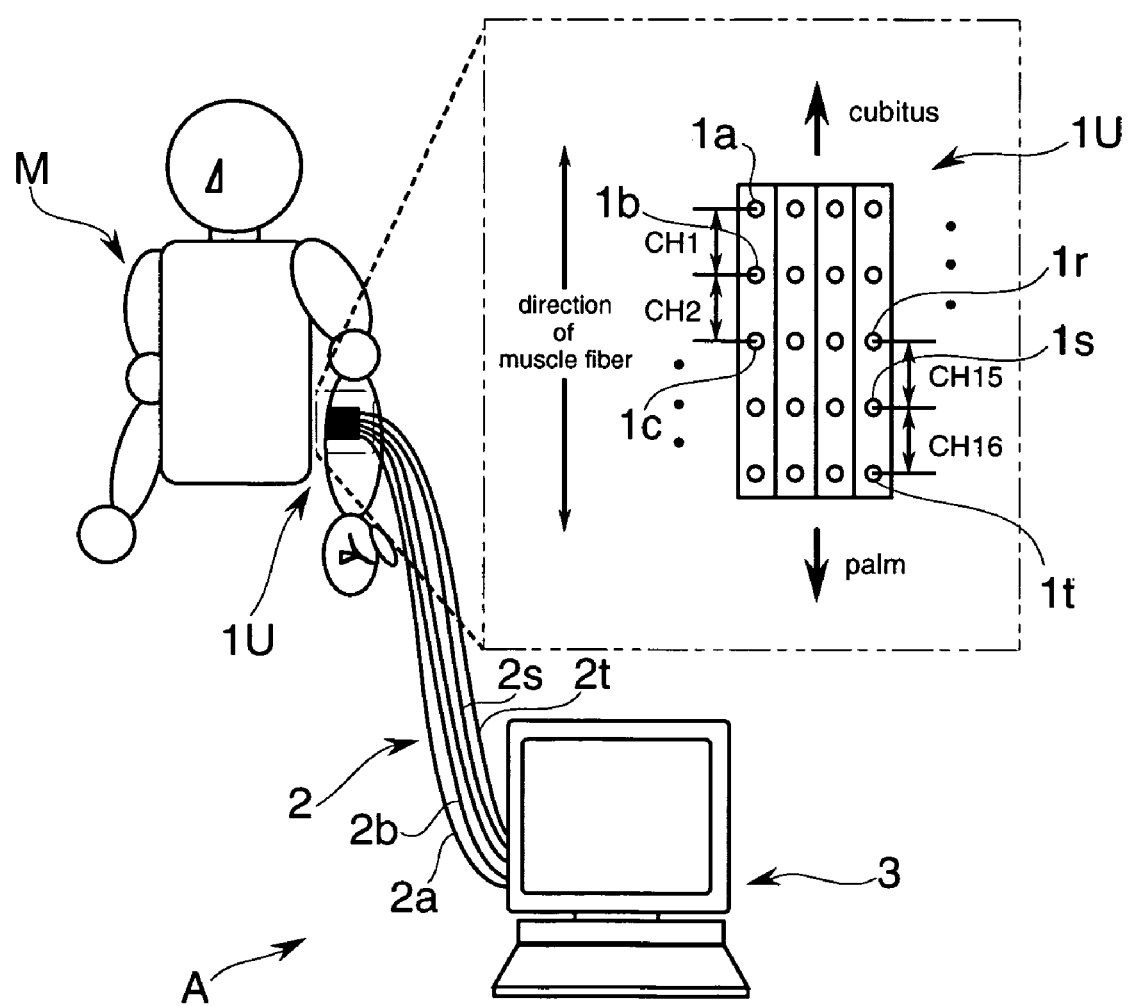
FIG. 1 is a pattern diagram of an overall structure of an active muscle display unit in accordance with an embodiment of the present claimed invention.

FIG. 1 is a view showing an overall structure of an active muscle display unit A in accordance with this embodiment of the present claimed invention.

The active muscle display unit A of this invention comprises a surface electrode unit 1U having multiple surface electrodes $1a$, $1b$, ..., $1s$, and $1t$ (hereinafter referred to as "surface electrodes 1"), multiple lead wires $2a$, $2b$, ..., $2s$, and $2t$ (hereinafter referred to as "lead wires 2") that are connected to the surface electrodes 1 respectively, and an active muscle display unit body 3 that is connected with the multiple lead wires 2 and that extracts a firing motor unit based on the surface electromyogram measured by the use of the multiple surface electrodes 1 and displays the extracted motor unit in an image. In this embodiment, an example of a case will be explained, wherein an arm of a subject M is placed on a table, not shown in drawings, that is horizontal to a ground surface, and an electromyogram is measured at a time of isometric contraction not accompanied by a change of a muscle length when a tensile force generates in the annular finger of the subject M and a firing motor unit is extracted based on the electromyogram and the extracted motor unit is displayed in an image.

Figure 2:
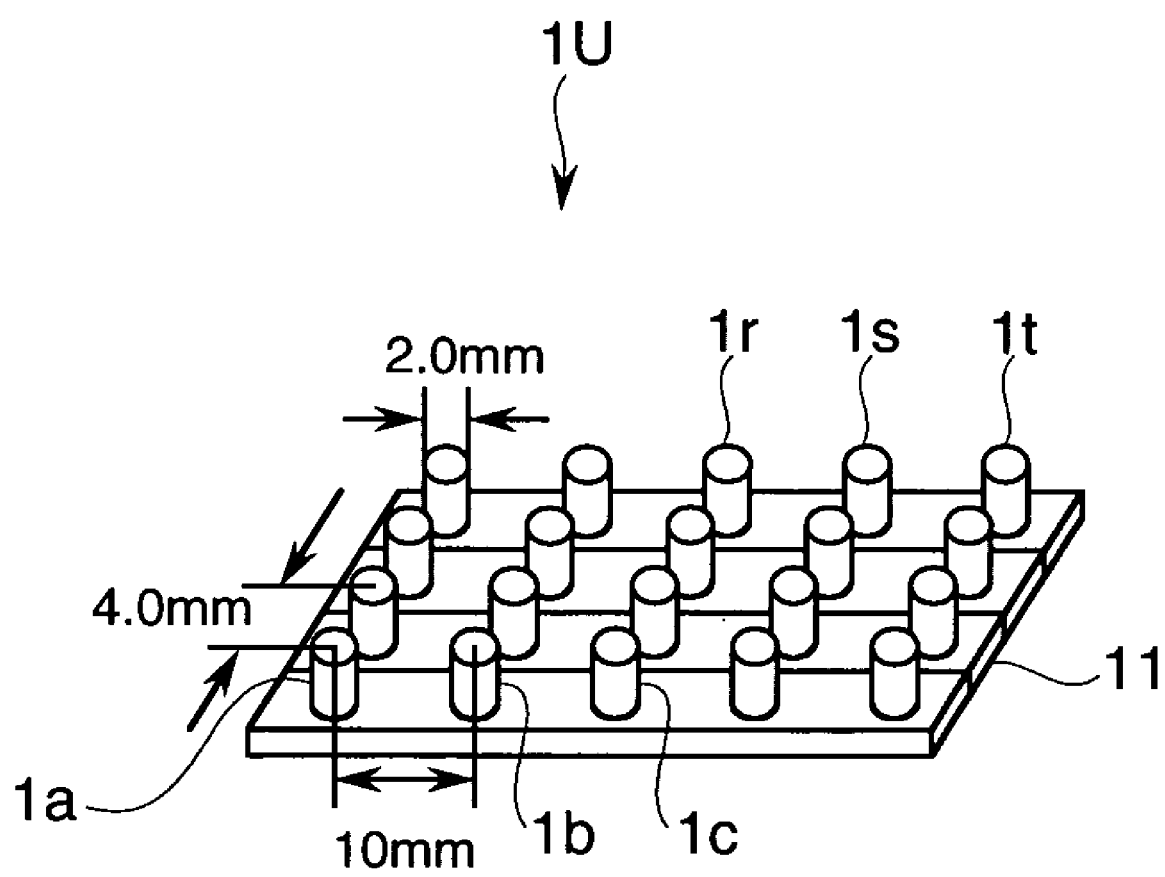
FIG. 2 is a pattern diagram of surface electrodes in accordance with this embodiment.

The surface electrode unit 1U comprises, as shown in FIG. 1 and FIG. 2, the surface electrodes 1 of 2.0 mm in diameter that detects a potential change on the skin surface generating in connection with a contraction movement of the muscle, and a surface electrode supporting plate 11 that mounts the surface electrodes 1 arrayed by 5×4 with each distance between electrodes of 10 mm and 4 mm. The surface electrode unit 1U is arranged at a position about 10 cm above the cubital fossa of the subject M so that the potential change on the skin surface generating in connection with the contraction movement of the muscle due to a movement of the annular finger is properly detected. In the surface electrodes 1 arrayed by 5×4, a pair of the surface electrodes 1 each of which is arranged side-by-side with the distance between electrodes 1 of 10 mm are set to be one channel and a difference in potential for each of the 16 channels is output to the active muscle display unit body 3 as a muscle potential signal.

Figure 3:
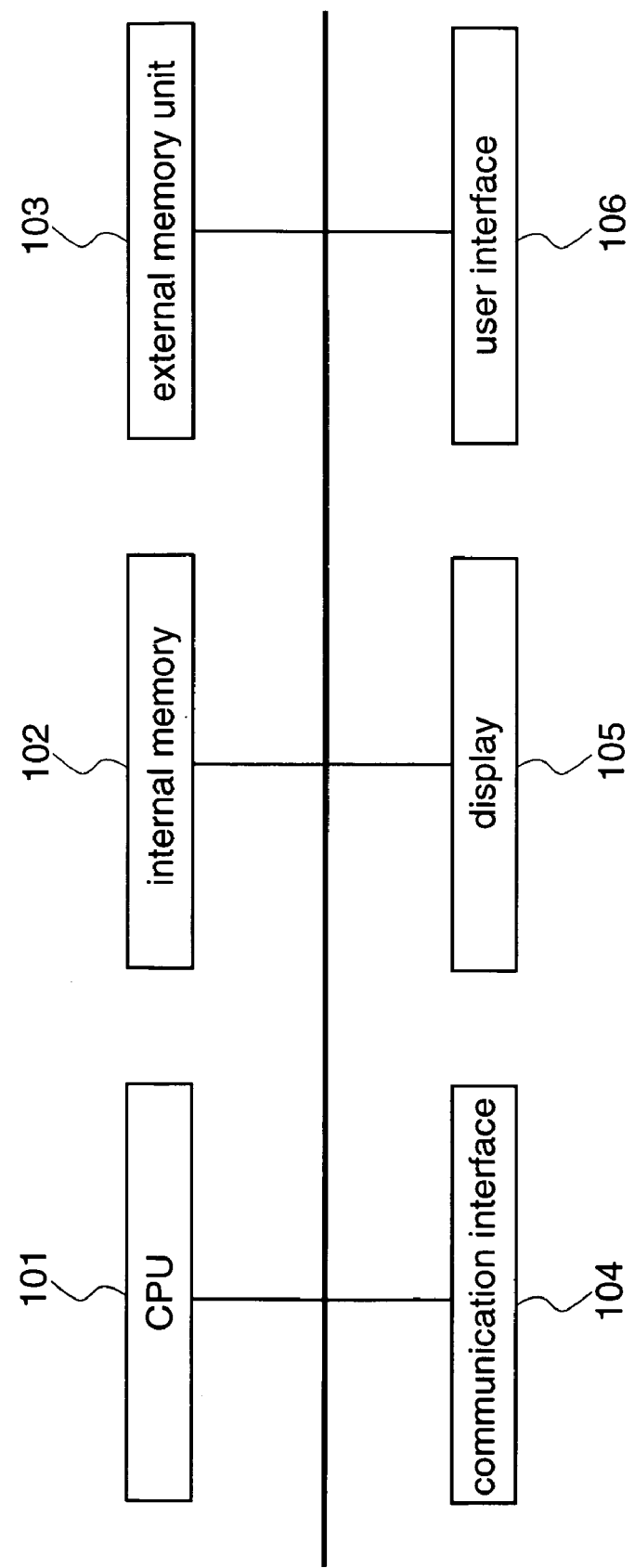
FIG. 3 is a structure view of an internal instrument of the active muscle display unit body in accordance with this embodiment.
Figure 4:
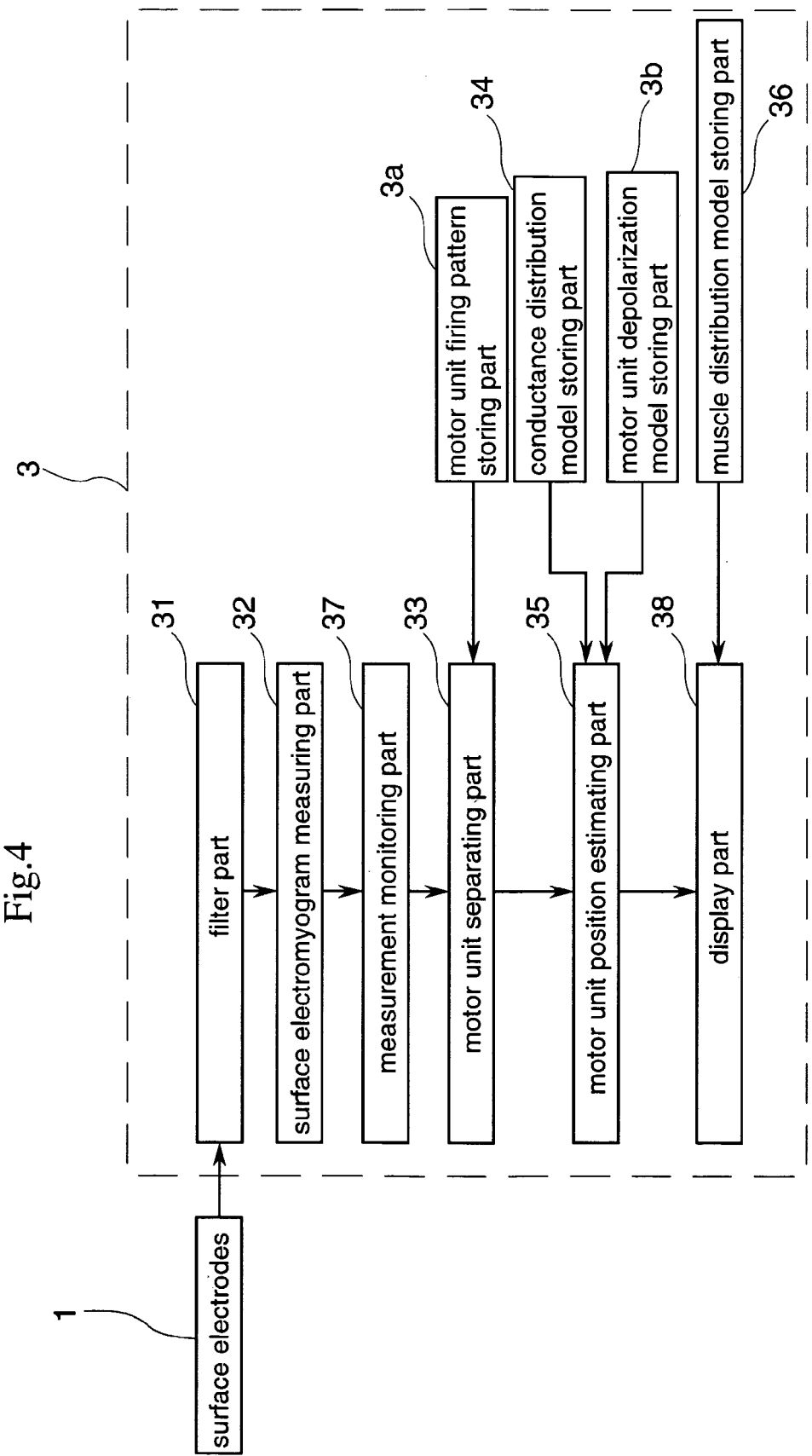
FIG. 4 is a functional structure view showing a function of, the active muscle display unit in accordance with this embodiment.

The active muscle display unit body 3 is a computer having a general information processing function and mainly comprises, as shown in FIG. 3, a CPU 101, an internal memory 102, an external memory unit 103 such as an HDD, a communication interface 104 connected with the lead wires 2, a display 105, and a user interface 106 such as a mouse or a keyboard.

The active muscle display unit body 3 is explained from a functional point of view. When each of the above mentioned components is operated, the active muscle display unit body 3 has functions of a filter part 31, a surface electromyogram measuring part 32, a motor unit separating part 33, a conductance distribution model storing part 34, a motor unit position estimating part 35, a muscle distribution model storing part 36, a measurement monitoring part 37, a display part 38, a motor unit firing pattern storing part 3a, a motor unit depolarization model storing part 3b and so on.

Next, each part will be described in detail.

Figure 5:
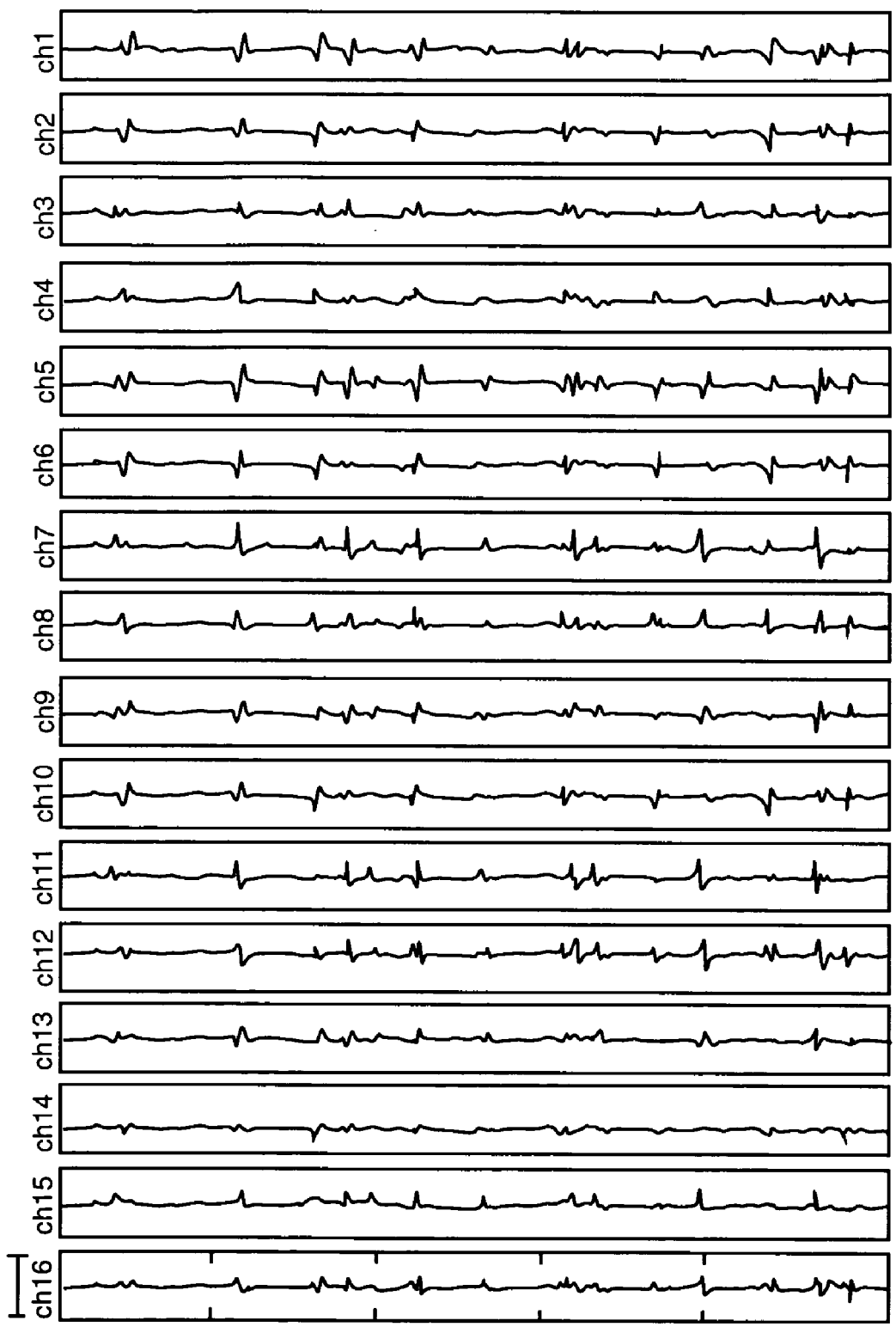
FIG. 5 is a view showing surface electromyogram for each channel in accordance with this embodiment.

The filter part 31 is to pass a frequency component whose frequency is higher than a predetermined frequency in a muscle potential signal obtained from the surface electrodes 1 through the lead wires 2. In this embodiment, the filter part 31 comprises a high-pass filter whose cutoff frequency is 2.5 Hz in order to preferably remove a change of a contact resistance due to a movement of skin and/or a fluctuation of a low frequency wave generating due to a swinging movement of the lead wires 2 from the muscle potential signal. The surface electromyogram for each of the sixteen channels is displayed, as shown in FIG. 5, on the display 105 after the frequency component of the muscle potential signal is passed through the filter part 31.

The surface electromyogram measuring part 32 measures the surface electromyogram on the skin surface after the muscle potential signal measured by the surface electrodes 1 is amplified and passed through an antialiasing filter. In this embodiment, the muscle potential signal is sampled with a sampling frequency of 1 kHz and an A/D conversion of 12 bit.

The motor unit separating part 33 estimates an individual motor unit constituting a firing muscle based on the surface electromyogram measured by the surface electromyogram measuring part 32. In this embodiment, the individual motor unit that shows a predetermined firing pattern is separated from the surface electromyogram measured by the surface electromyogram measuring part 32 by means of a multichannel blind deconvolution method.

The multichannel blind deconvolution method will be explained more concretely. This method is one of the techniques to be classified into an independent component analysis that can separate a signal into a statistically independent component by making use of a higher statistics value. In accordance with this method, when a signal at each time t for multi-channels monitored-as being mixing filtered time independent signal $s(t)=[s_1(t), \ldots, s_n(t)]^T$ is expressed by $x(t)=[x_1(t), \ldots, x_n(t)]^T$, the signal can be separated into an independent component $y(t)=[y_1(t), \ldots, y_n(t)]^T$ by the expression (1).

$$y(t) = W(Z^{-1})x(t) \quad (1)$$

Then $W(Z^{-1})$ is shown by the expression (2).

$$W_{ij}(Z^{-1}) = \sum_{\tau'=-\tau}^{\tau} W_{ij}(\tau')z^{-\tau'} \quad (2)$$

Where $Z^{-1}$ shows a time delay operator that acts as $$Z^{-\tau}x(t)=x(t-\tau).$$

Figure 6:
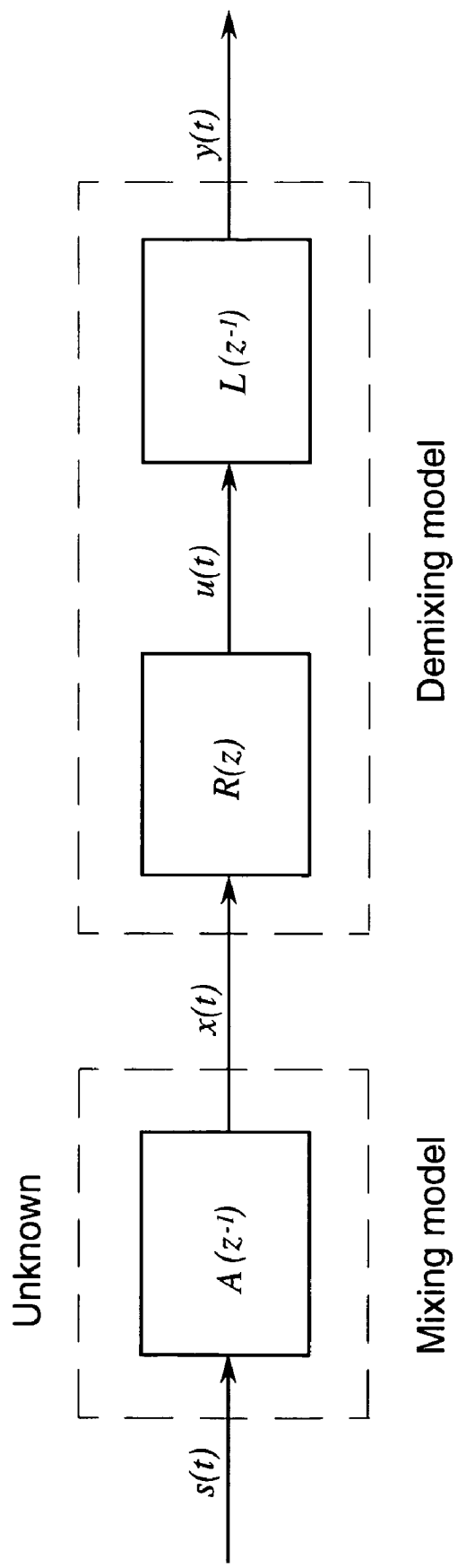
FIG. 6 is a view showing a structure of blind deconvolution in accordance with this embodiment.

In order to make it easy to obtain an inverse filter, $W(Z^{-1})$ is separated into two one-sided filters; FIR filters L (causal) and R (non-causal). A process of blind deconvolution in the separated filter is shown in FIG. 6. The mixing filter is assumed to be constant in terms of time and space, then an estimation of its inverse filter is learned by the following expressions (3) and (4).

$$\Delta L(\tau) = \eta \sum_{\tau'=0}^{\tau} \{\delta(\tau') - \varphi(y(t))y^T(t-\tau')\}L(\tau-\tau') \quad (3)$$

$$\Delta R(\tau) = -\eta \sum_{\tau'=0}^{\tau} L^H(z^{-1})\varphi(y(t))u^T(t+\tau')R(\tau-\tau') \quad (4)$$

Where R(0) is a unit matrix expressed by the following expression.

$$L^H(z^{-1}) = \sum_{\tau=0}^{N} L(\tau)^T z^\tau$$

Figure 9:
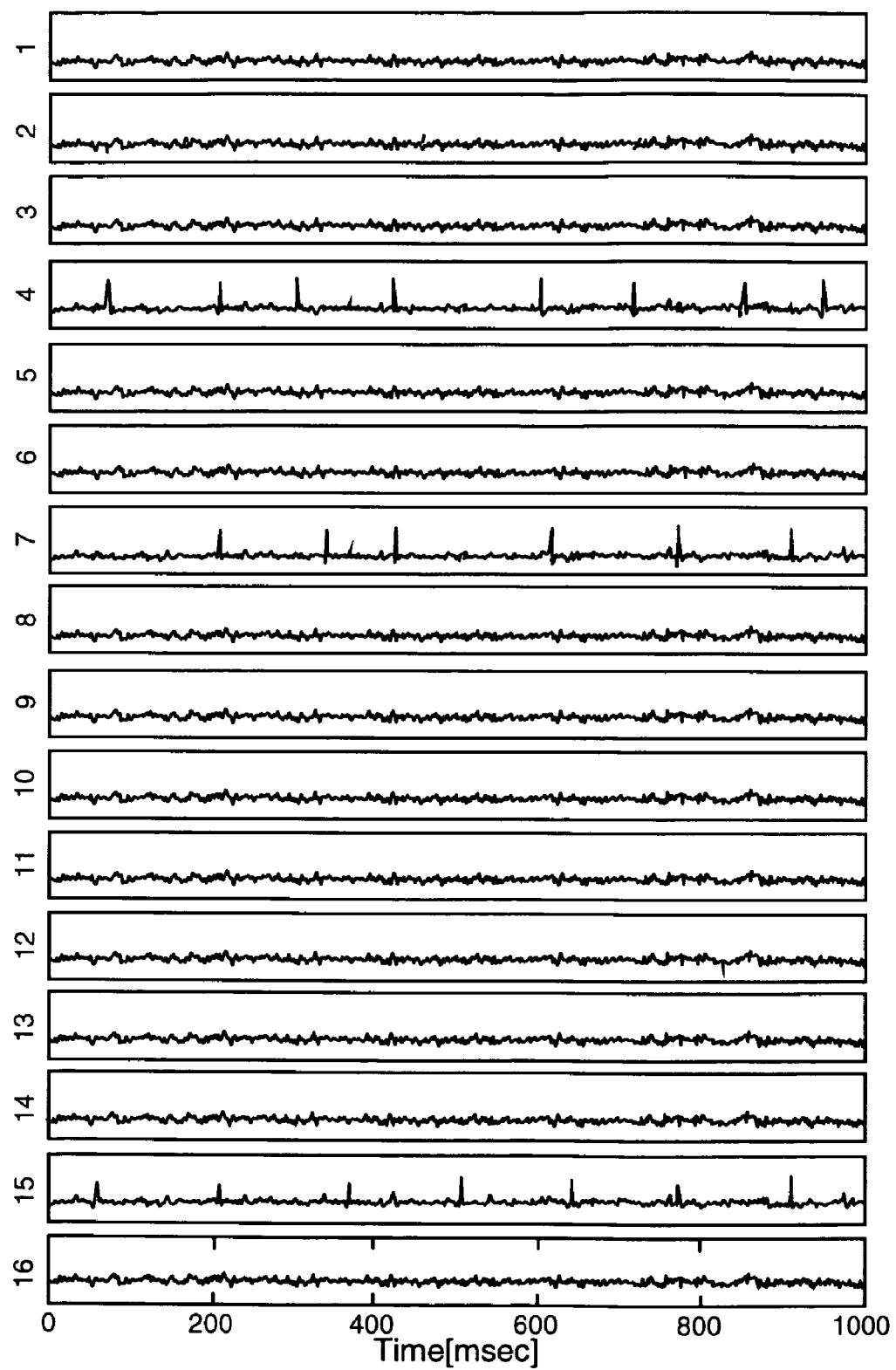
FIG. 9 is an example of each output signal of the independent component in accordance with this embodiment.

An example of each output signal of the independent component separated by the above process is shown in FIG. 9. In this example, a signal corresponding to a single motor unit is shown in the fourth, the seventh, and the fifteenth components. The signal is displayed on the display and a person in charge of measurement selects the signal.

Figure 10:
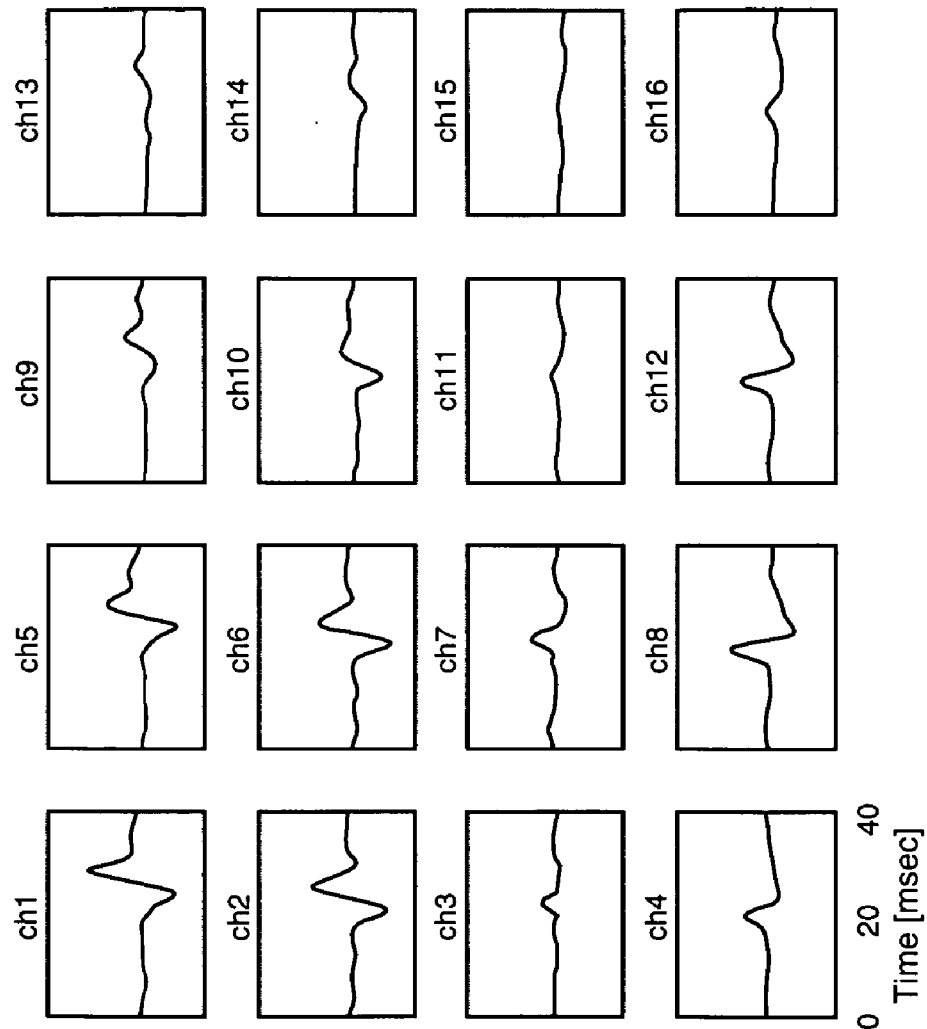
FIG. 10 is a view showing an impulse response of a mixing filter to a fourth independent component in accordance with this embodiment.
Figure 11:
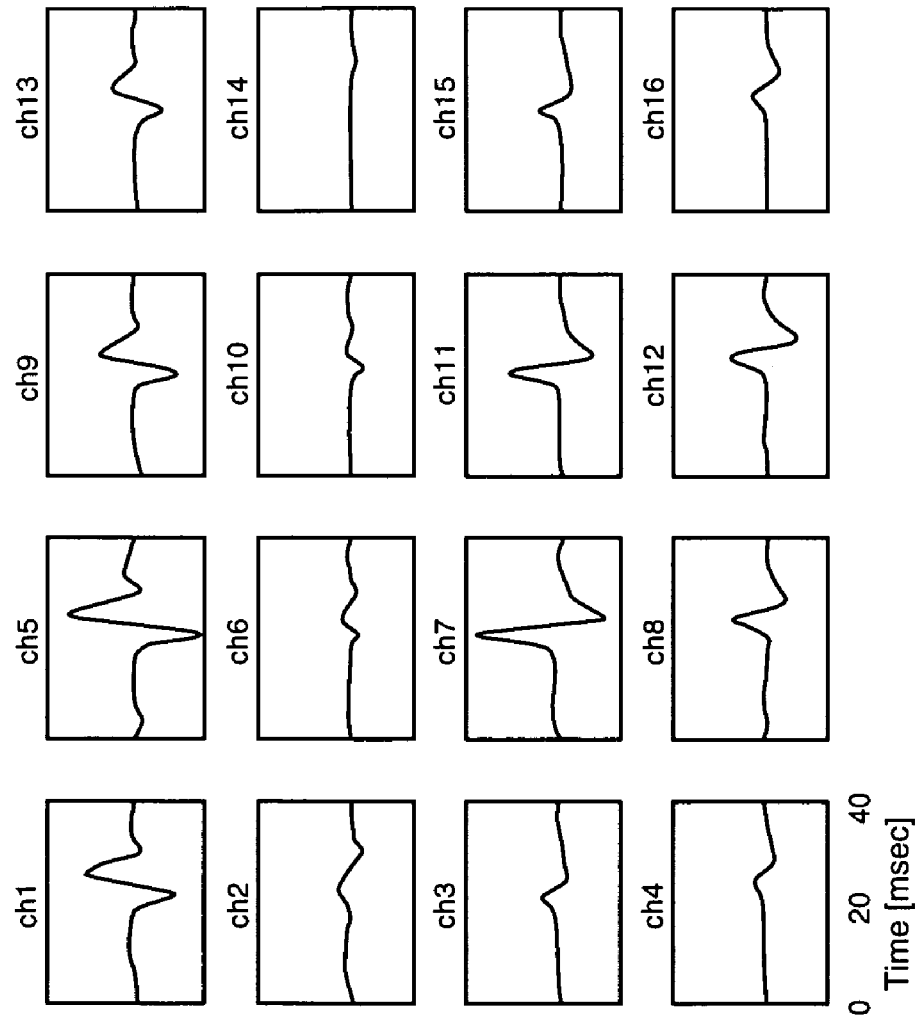
FIG. 11 is a view showing an impulse response of the mixing filter to a seventh independent component in accordance with this embodiment.
Figure 12:
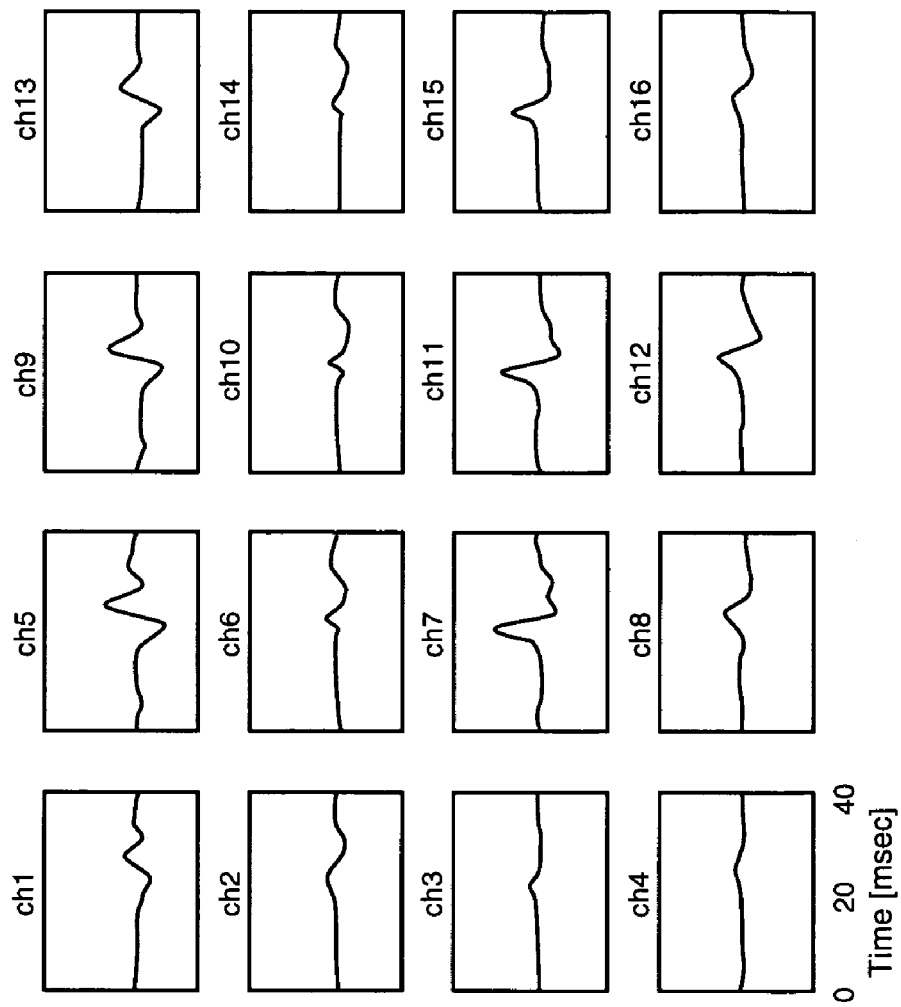
FIG. 12 is a view showing an impulse response of the mixing filter to a fifteenth independent component in accordance with this embodiment.

Next, how an MUAP corresponding to each independent component appears on each surface electrode is checked as follows. Only an impulse output of the "i"th independent component is expressed by $y=[0, \ldots, 0, y_i(t), 0, \ldots, 0]^T$, and an input x(i) to $y_i(t)=[0, \ldots, 0, \delta(t), 0, \ldots, 0]$ is expressed by the expression (5) due to $y(t)=W(Z^{-1})x(t)$.

$$x(i)=W(Z^{-1})^{-1} \text{ of the "i"th column} \quad (5)$$

Where δ(t) is 1 only when t=0, and δ(t) is 0 when t is otherwise. This is an impulse response showing how the MUAP generating from the motor unit corresponding to the "i"th independent component is input on each surface electrode. The impulse responses calculated by the expression (5) to the fourth, the seventh, the fifteenth independent components and the impulse response calculated by the expression (5) to the sixteenth independent component for comparison that is estimated as being different from the motor unit are shown in FIG. 10 through FIG. 13. The results shown in FIG. 10 through FIG. 12 are consistent with the impulse response corresponding to the single motor unit. However, the result shown in FIG. 13 tells that an especially significant signal is not separated. When the impulse responses shown in FIG. 10 through FIG. 12 are monitored, it is confirmed that a phase of the impulse response at an electrode arranged upper side near the cubitus of the subject M is reversed from a phase of the impulse response at an electrode arranged downside near a distal end of a hand of the subject M. Since the MUAP is propagated from the motion end plate to both ends of the muscle fiber, it is known that the phases of each electromyogram in front of and behind the motion end plate are reversed. As a result, the reason why an electrode whose impulse response of the motor unit is very week exists at a portion where a phase is reversed is conceived that the motion end plate exists near the electrodes. In addition, since a position of the motion end plate and a position of the electrode where the maximum amplitude is shown vary respectively with respect to each of the impulse responses shown in FIG. 10, FIG. 11 and FIG. 12, each of the impulse responses shown in FIG. 10, FIG. 11 and FIG. 12 can be conceived to extract the different motor unit. At the same time, since no especially distinguished characteristic can be seen in respect to the sixteenth independent component shown in FIG. 13, the sixteenth independent component can be considered to be extracted as a noise. As mentioned above, the fourth, the seventh, and the fifteenth independent components can be specified as the motor unit from a view point of a characteristic of the mixing filter through which the independent components pass.

The firing motor unit is separated based on the surface electromyogram measured by the surface electromyogram measuring part 32 by the use of the multichannel blind deconvolution method. In this embodiment, as a learning condition to conduct the multichannel blind deconvolution method, it is set that a number of taps τ is 20, a patch size is 100, and a learning rate begins with η(0)=0.00001 and is updated in accordance with η(t+1)=0.8η(t) with respect to every 10 times. In addition, a nonlinear function φ(x) uses φ(x)=tanh (x) by presumption that a firing statistics of the motor unit is a super Gaussian distribution. The super Gaussian distribution is a distribution wherein a quartic statistics amount of $K=E[(x-\mu)^4]/E[(x-\mu^2)^2]-3$ referred to as a kurtosis takes a positive value.

Figure 7:
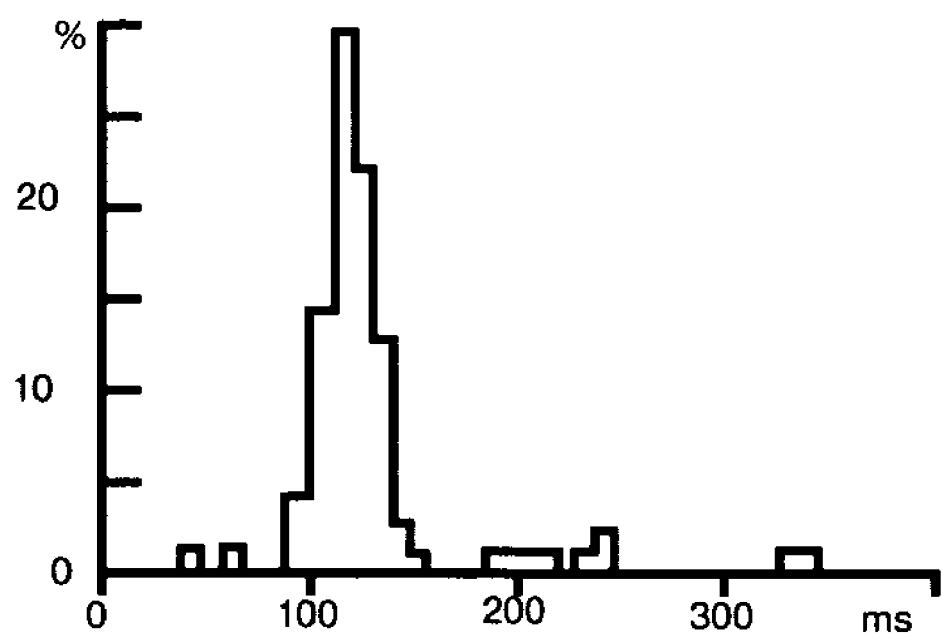
FIG. 7 is a view showing a distribution pattern of a firing interval of a motor unit stored in a firing interval distribution pattern storing part in accordance with this embodiment.

The motor unit firing pattern storing part 3a stores a distribution pattern of a firing interval of the motor unit based on the physiological knowledge and is formed in a predetermined area of the external memory unit 103 or the internal memory 102. In this embodiment, the distribution pattern of the firing interval of the motor unit based on the physiological knowledge is obtained, as shown in FIG. 7, from a needle electromyogram that can be shown as a distribution of the firing interval of the motor unit.

The motor unit position estimating part 35 solves an inverse problem given by the Poison equation $\nabla \cdot \sigma \nabla \phi = -I$ as being a partial differential equation concerning an electrostatic field and obtains a distribution of a current source I corresponding to the individual motor unit respectively with a boundary condition of a potential on each electrode resulting from the individual motor unit separated by the motor unit separating part 33. Where σ is a conductance distribution of a living organism tissue and given by the conductance distribution model storing part 34, φ is a potential distribution in the living organism tissue and meets the boundary condition $\sigma \nabla \phi \cdot n = 0$ on the skin surface, and n is a normal line vector to the skin.

The distribution of the current source I to the individual motor unit obtained by the motor unit position estimating part 35 shows a depolarization position of the muscle fiber constituting the individual motor unit in the living organism tissue, however, its inverse problem is an ill-posed problem, thereby being unable to determine a solution to the inverse problem uniquely. As a result, a motor unit depolarization model that is modeled how the motor unit is depolarized to generate the action potential is previously stored in the motor unit depolarization model storing part 3b and the solution is determined-uniquely by making use of the motor unit depolarization model.

The muscle distribution model storing part 36 stores a muscle distribution model that is a modeled muscle fiber or a modeled motor neuron constituting the motor unit and is formed in a predetermined area of the external memory unit 103 or the internal memory 102.

The measurement monitoring part 37 outputs a measuring surface electromyogram at a time of measuring the surface electromyogram to the display 105 in an image. In this embodiment, the surface electromyogram measuring part 32 is set not to conduct a measurement in case that the surface electromyogram estimated as other than the motor unit is output to the display 105 while the surface electromyogram is measured.

The display part 38 outputs a depolarization position of the motor unit estimated by the motor unit position estimating part 35 in a state overlapped with the muscle distribution model stored in the muscle distribution model storing part 36 to the display 105 in three-dimensional images.

Figure 8:
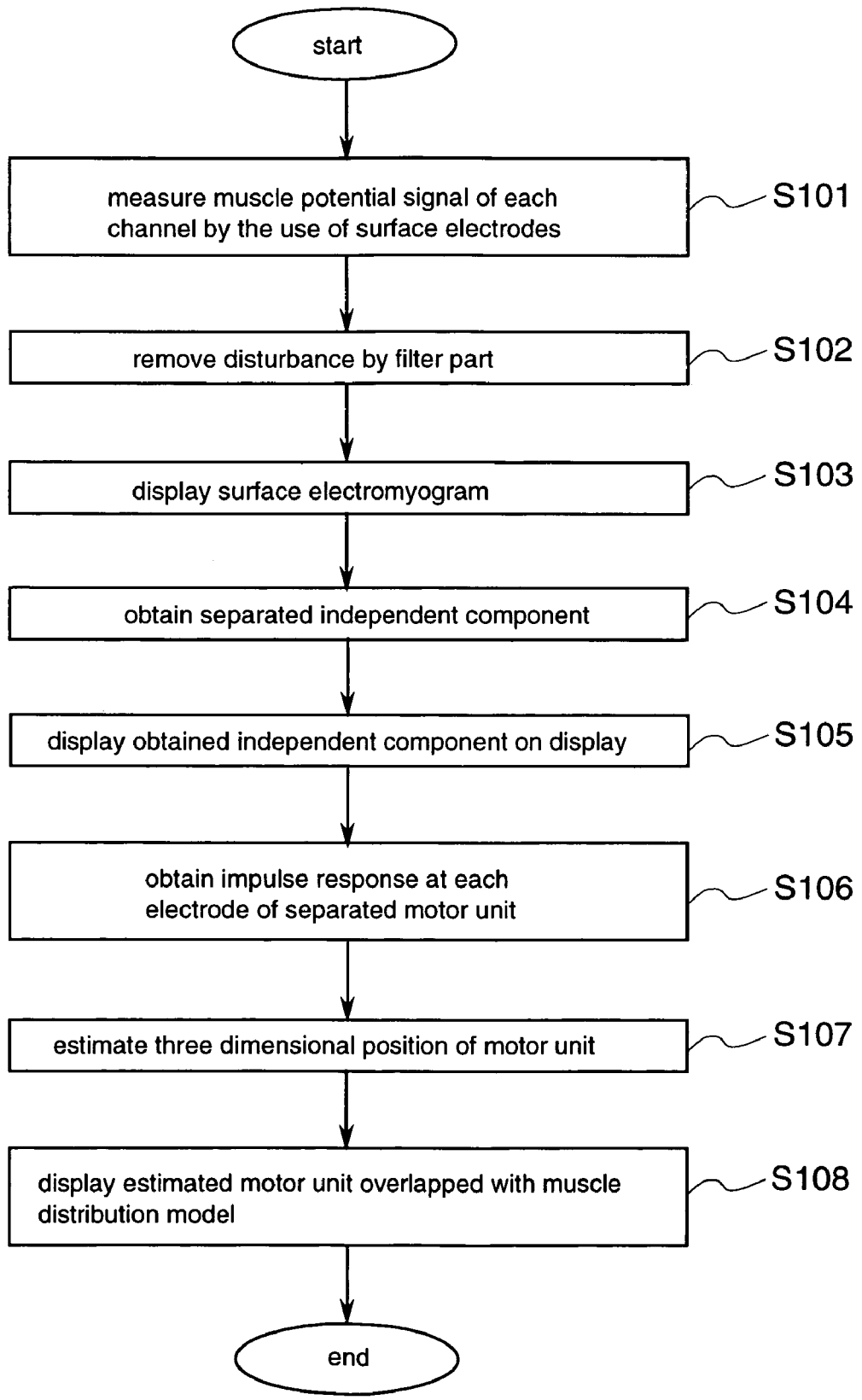
FIG. 8 is a flow chart showing a movement of the active muscle display unit in accordance with this embodiment.

Next, an operation of the active muscle display unit A of the above arrangement will be explained with reference to a flow chart shown in FIG. 8. In this embodiment, the active muscle display unit A is set to conduct a main operation after preparation is made with the procedures of (1) through (4). (1) The subject M is seated on a chair and the left arm of the subject M is fixed on a table with his or her palm facing upward. (2) A person in charge of measurement confirms that there is no noise except for hum noise in a signal of each channel and that the hum noise is adequately minimized. (3) The person in charge of measurement gives an instruction to the subject M to put a force into a predetermined finger with a certain amount of force while monitoring the electromyogram displayed on the display 105. (4) The subject M puts the certain amount of force into the predetermined finger with a cue from the person in charge of measurement.

First, when a myoelectric signal is measured for each channel by the use of the surface electrodes 1 (Step S101), disturbance such as a change of a contact resistance due to a movement of a skin and a fluctuation of a low frequency generating due to a swinging movement of the lead wires 2 is removed by the filter part 31 (Step S102) and the myoelectric signal passing the filter part 31 is displayed on the display 105 as a surface electromyogram measured for each channel as shown in FIG. 5 (Step S103). Next, the motor unit separating part 33 obtains an independent component separated from the electromyogram shown in FIG. 5 by the use of the multi-channel deconvolution method (Step S104), and displays the independent component on the display 105 as shown in FIG. 9. The fourth, the seventh and the fifteenth components, whose amplitude of the peak value and a firing cycle of the independent component generally coincide with each other among the independent components displayed on the display 105, are estimated as the motor unit (Step S105). In this embodiment, the estimation of the independent component is set to select a component which the person in charge of measurement estimates as being an independent component from the surface electromyogram displayed on the display 105 and to input the motor unit estimated to fire by making use of the user interface 106 into the active muscle display unit body 3. Next, the impulse response of the separated motor unit at each electrode is obtained (Step S106), and the three dimensional position of the motor unit is estimated with the obtained impulse response considered as the boundary condition (Step S107).

The motor unit X whose position has been specified is displayed by the display part 38 on the display 105 in a state overlapped with the muscle distribution model stored in the muscle distribution model storing part 36 (Step S108). In this embodiment, as shown in FIG. 14, a three-dimensional structure image of a tissue of the arm taken by the fMRI is displayed on the display 105 in a translucent state and the motor unit X whose position has been specified is set to be displayed by a bright line (slash mark in FIG. 14).

As mentioned above, in accordance with the active muscle display unit A of this embodiment, since the surface electromyogram can be measured by multiple surface electrodes and the surface electromyogram measuring part 32 without invading the living organisms, the firing motor unit can be separated from the multiple spatially and temporally added MUAPs by the motor unit separating part 33 and the motor unit position estimating part 35, and the motor unit whose position has been specified can be displayed in an image on the display, the active muscle display unit A is very useful for analyzing a control mechanism of living organisms.

In addition, since it is possible to preferably remove the disturbance such as the change of the contact resistance due to the movement of the skin or the fluctuation of the low frequency generating due to the swinging movement of the lead wire, the surface electromyogram can be measured with accuracy and the firing motor unit can be extracted.

Furthermore, since the motor unit that has been specified as being firing is displayed in the state overlapped with the muscle distribution model, it is possible to recognize the movement of the muscle more concretely.

In this embodiment, explained as the example is the case wherein the arm of the subject M is placed on the table, not shown in drawings, that is horizontal to the ground surface, the surface electromyogram is measured at the time of isometric contraction not accompanied by the change of the muscle length when the tensile force generates in the annular finger of the subject M, and the firing motor unit is extracted based on the surface electromyogram and then the extracted motor unit is displayed in an image, however, it is a matter of course that a portion other than the annular finger may be measured and the firing motor unit may be extracted and displayed in an image.

In addition, the firing motor unit can be extracted and displayed in an image at a time not limited to a case of isometric contraction not accompanied by a change of a muscle length but may be a case of isometric contraction accompanied by a change of a muscle length.

In addition, the cut-off frequency of the high-pass filter is set to 2.5 Hz in this embodiment, however, it is not limited to this.

In this embodiment, the surface electrodes 1 are arranged in an arrayed form by 5×4 with each distance between electrodes of 10 mm and 4 mm, however, the number of the arranged surface electrodes 1 and the arranged form of the surface electrodes 1 are not limited to this, and a shape or a size of the used surface electrodes 1 may be set arbitrarily.

In this embodiment, it is set that the person in charge of measurement selects the surface electromyogram estimated as the independent component from the surface electromyogram displayed on the display 105, and the motor unit estimated to be the firing motor unit is input to the motor unit separating part 33 by the use of the user interface 106, however, the estimation may be specified automatically by the active muscle display unit body 3.

Other concrete arrangement of each component is not limited to the above-mentioned embodiment, and there may be various modifications without departing from a spirit of the present claimed invention.

POSSIBLE APPLICATIONS IN INDUSTRY

As mentioned above, in accordance with the present claimed invention, since the surface electromyogram can be measured by multiple surface electrodes and the surface electromyogram measuring part without invading living organisms, a three dimensional position of the active motor unit can be extracted from the multiple spatially and temporally added MUAPs by the motor unit separating part and the motor unit position estimating part, and the extracted motor unit can be displayed in an image by the display part, the active muscle display unit is very useful for analyzing a control mechanism of a muscle in a living organisms.

The invention claimed is:

1. An active muscle display unit comprising:
multiple electrodes that are adapted to be arranged on the skin surface,
a surface electromyogram measuring part that measures a surface electromyogram on the skin surface at the multiple electrodes,
a motor unit separating part that estimates an individual motor unit constituting an active muscle and showing a predetermined firing pattern, based on the surface electromyogram measured by the surface electromyogram measuring part,
a motor unit position estimating part that estimates a position of a firing motor unit, based on the individual motor unit estimated to constitute the active muscle by the motor unit separating part, and
a display part that displays the individual motor unit estimated by the motor unit position estimating part in an image.

2. The active muscle display unit described in claim 1, wherein the motor unit separating part estimates the individual motor unit from the surface electromyogram measured by the surface electromyogram measuring part, based on a multi-channel blind deconvolution method.

3. The active muscle display unit described in claim 1, further comprising a motor unit firing pattern storing part that stores a distribution pattern of a firing interval and a surface electromyogram waveform of the individual motor unit based on physiological knowledge based on firing statistics of the motor unit or potential distribution formed by depolarization of a muscle fiber,
wherein a time-series signal of each of said multiple electrodes separated by the motor unit separating part is checked against the individual motor unit whose distribution pattern of the firing interval and the surface electromyogram waveform are stored, and
wherein if a distribution pattern of a firing interval and a surface electromyogram waveform of the time-series signal coincide with the stored distribution pattern of the firing interval and the stored surface electromyogram waveform, the time-series signal is specified as the individual motor unit.

4. The active muscle display unit described in claim 1, wherein the motor unit position estimating part solves an inverse problem of a partial differential equation representing an electrostatic field to reproduce an electrode position potential of the individual motor unit based on an electrode position potential corresponding to the individual motor unit obtained by the motor unit separating part.

5. The active muscle display unit described in claim 1, wherein the motor unit position estimating part estimates a current source using Poisson's equation to reproduce a potential of the individual motor unit based on an electrode position potential corresponding to the individual motor unit obtained by the motor unit separating part.

6. The active muscle display unit described in claim 1, further comprising a conductance distribution model storing part that stores a conductance distribution model,
wherein distribution and arrangement of fat, bone, and muscle whose electrical conductance differs respectively in vivo, are modeled so that the motor unit position estimating part can solve an inverse problem.

7. The active muscle display unit described in claim 1, further comprising a motor unit depolarization model storing part that stores a depolarization mode of a motor unit so that the motor unit position estimating part can solve an inverse problem uniquely.

8. The active muscle display unit described in claim 1, wherein said multiple electrodes are arranged in an array.

9. The active muscle display unit described in claim 1, further comprising a high-pass filter that passes a signal having a frequency component not less than a predetermined frequency,
- wherein the surface electromyogram measured by the surface electromyogram measuring part is passed through the high-pass filter.

10. The active muscle display unit described in claim 1, wherein the surface electromyogram measured by the surface electromyogram measuring part is normalized to an average of 0, and a distribution of 1.

11. The active muscle display unit described in claim 1, wherein the motor unit separating part learns the surface electromyogram measured by the surface electromyogram measuring part under a predetermined condition and estimates the individual motor unit constituting the firing muscle based on the learned surface electromyogram.

12. The active muscle display unit described in claim 1, further comprising a muscle distribution model storing part that stores a muscle distribution model, in which a muscle fiber or a motor neuron constituting the individual motor unit is modeled, and
- wherein the display part displays the individual motor unit extracted by the motor unit position estimating part in an overlapped state with the muscle distribution model.

13. The active muscle display unit described in claim 1, further comprising:
- a measurement monitoring part that outputs the surface electromyogram in the image, while the surface electromyogram is measured,
- wherein when the surface electromyogram which is output in the image is determined not to be derived from the firing motor unit, the surface electromyogram measuring part stops conducting the measurement of the surface electromyogram.

* * * * *